US011744881B2

(12) United States Patent
Williams

(10) Patent No.: US 11,744,881 B2
(45) Date of Patent: *Sep. 5, 2023

(54) TREATMENT OF AMYOTROPHIC LATERAL SCLEROSIS USING BOTULINUM TOXIN

(71) Applicant: PENLAND FOUNDATION, Beaumont, TX (US)

(72) Inventor: Roland M. Williams, Beaumont, TX (US)

(73) Assignee: PENLAND FOUNDATION, Beaumont, TX (US)

( * ) Notice: Subject to any disclaimer, the term of this patent is extended or adjusted under 35 U.S.C. 154(b) by 91 days.

This patent is subject to a terminal disclaimer.

(21) Appl. No.: 17/215,082

(22) Filed: Mar. 29, 2021

(65) Prior Publication Data
US 2021/0299231 A1 Sep. 30, 2021

Related U.S. Application Data

(63) Continuation of application No. 17/204,922, filed on Mar. 17, 2021, and a continuation of application No. 16/995,042, filed on Aug. 17, 2020, now Pat. No. 11,241,479, and a continuation of application No. 16/875,951, filed on May 15, 2020, now Pat. No. 11,090,371, and a continuation of application No. 16/875,947, filed on May 15, 2020, now Pat. No. 10,960,061, and a continuation of application No. 16/875,924, filed on May 15, 2020, now Pat. No. 10,973,873, said application No. 17/204,922 is a continuation of application No. 16/875,912, filed on May 15, 2020, now Pat. No. 10,967,052, application No. 17/215,082 is a continuation of application No. 16/875,945, filed on May 15, 2020, now Pat. No. 10,960,060, and a continuation of application No. 16/875,935, filed on May 15, 2020, now Pat. No. 10,987,411, said application No. 16/875,912 is a continuation-in-part of application No. 16/657,933, filed on Oct. 18, 2019, now Pat. No. 10,722,552, said application No. 16/875,951 is a continuation-in-part of application No. 16/657,933, filed on Oct. 18, 2019, now Pat. No. 10,722,552, said application No. 16/875,935 is a continuation-in-part of application No. 16/657,950, filed on Oct. 18, 2019, now abandoned, said application No. 16/875,924 is a continuation-in-part of application No. 16/657,933, filed on Oct. 18, 2019, now Pat. No. 10,722,552, said application No. 16/875,945 is a continuation-in-part of application No. 16/657,950, filed on Oct. 18, 2019, now abandoned, said application No. 16/875,924 is a continuation-in-part of application No. 16/657,950, filed on Oct. 18, 2019, now abandoned, said application No. 16/875,951 is a continuation-in-part of application No. 16/657,950, filed on Oct. 18, 2019, now abandoned, said application No. 16/875,947 is a continuation-in-part of application No. 16/657,950, filed on Oct. 18, 2019, now abandoned, said application No. 16/875,935 is a continuation-in-part of application No. 16/657,933, filed on Oct. 18, 2019, now Pat. No. 10,722,552, said application No. 16/995,042 is a continuation of application No. 16/657,950, filed on Oct. 18, 2019, now abandoned, said application No. 16/875,947 is a continuation-in-part of application No. 16/675,933, filed on Oct. 18, 2019, now Pat. No. 10,722,552, said application No. 16/875,912 is a continuation-in-part of application No. 16/657,950, filed on Oct. 18, 2019, now abandoned, said application No. 16/875,945 is a continuation-in-part of application No. 16/657,933, filed on Oct. 18, 2019, now Pat. No. 1,072,552.

(51) Int. Cl.
*A61K 38/48* (2006.01)
*A61K 9/00* (2006.01)

(52) U.S. Cl.
CPC ........ *A61K 38/4893* (2013.01); *A61K 9/0019* (2013.01); *C12Y 304/24069* (2013.01)

(58) Field of Classification Search
None
See application file for complete search history.

(56) References Cited

U.S. PATENT DOCUMENTS

| 5,766,605 A | 6/1998 | Sanders et al. |
| 6,063,768 A | 5/2000 | First |
| 6,139,845 A | 10/2000 | Donovan |
| 6,143,306 A | 11/2000 | Donovan |

(Continued)

FOREIGN PATENT DOCUMENTS

| EP | 2072039 A1 | 6/2009 |
| JP | 2007509953 A | 4/2007 |

(Continued)

OTHER PUBLICATIONS

Wijesekera, Orphanet Journal of Rare Diseases 2009, 4:3 doi:10.1186/1750-1172-4-3 (Year: 2009).*

(Continued)

*Primary Examiner* — Christina M Borgeest
(74) *Attorney, Agent, or Firm* — Fox Rothschild LLP

(57) ABSTRACT

A method for treating Amyotrophic Lateral Sclerosis (ALS), also known as motor neuron disease (MND) or Lou Gehrig's disease, in a patient in need thereof comprises administering botulinum toxin to the patient. The botulinum toxin may be administered by subcutaneous or intradermal injection. The injection may be administered to and/or around the vicinity of a trigeminal nerve, a cervical nerve, a thoracic nerve, a lumbar nerve, and/or a sacral nerve of the patient. The administration of the botulinum toxin prevents an overproduction of glutamate, Substance P, and CGRP in a sensory system and thereby inhibits a migration of the glutamate, Substance P, and CGRP to the motor system, which otherwise would cause neuroexcitatory toxicity that results in the death of motor neurons.

20 Claims, No Drawings

(56) References Cited

U.S. PATENT DOCUMENTS

| | | |
|---|---|---|
| 6,261,572 B1 | 7/2001 | Donovan |
| 6,337,075 B1 | 1/2002 | Donovan |
| 6,632,440 B1 | 10/2003 | Quinn et al. |
| 6,977,080 B1 | 12/2005 | Donovan |
| 7,655,244 B2 | 2/2010 | Blumenfeld |
| 8,470,337 B2 | 6/2013 | Manack et al. |
| 8,734,810 B2 | 5/2014 | Blumenfeld |
| 8,852,163 B2 | 10/2014 | Deem et al. |
| 8,972,004 B2 | 3/2015 | Simon et al. |
| 9,254,314 B2 | 2/2016 | Finzi et al. |
| 9,707,207 B2 | 7/2017 | Finegold |
| 10,011,823 B2 | 7/2018 | Barbieri et al. |
| 10,258,673 B2 | 4/2019 | Pokushalov et al. |
| 10,722,552 B1 | 7/2020 | Williams |
| 10,960,061 B1 | 3/2021 | Williams |
| 10,973,873 B1 | 4/2021 | Williams |
| 10,987,441 B1 | 4/2021 | Sykes |
| 2001/0012828 A1 | 8/2001 | Aoki et al. |
| 2004/0062776 A1 | 4/2004 | Voet |
| 2004/0213815 A1 | 10/2004 | Ackerman |
| 2004/0220544 A1 | 11/2004 | Heruth et al. |
| 2005/0147626 A1 | 7/2005 | Blumenfeld |
| 2005/0191320 A1 | 9/2005 | Turkel et al. |
| 2007/0259002 A1 | 11/2007 | Batchelor |
| 2009/0142430 A1 | 6/2009 | Sanders et al. |
| 2009/0232850 A1 | 9/2009 | Manack et al. |
| 2010/0303788 A1 | 12/2010 | Francis et al. |
| 2011/0200639 A1 | 8/2011 | Blumenfeld |
| 2012/0093827 A1 | 4/2012 | Van Schaack et al. |
| 2012/0195878 A1 | 8/2012 | Haag-Molkenteller et al. |
| 2012/0244188 A1 | 8/2012 | Blumenfeld et al. |
| 2012/0251519 A1 | 10/2012 | Blumenfeld et al. |
| 2013/0251830 A1 | 9/2013 | Manack et al. |
| 2014/0099298 A1 | 4/2014 | Blumenfeld |
| 2015/0086533 A1 | 3/2015 | Borodic |
| 2016/0095908 A1 | 4/2016 | Borodic et al. |
| 2017/0173123 A1 | 6/2017 | Blumenfeld |
| 2017/0333537 A9 | 11/2017 | Borodic |
| 2018/0071361 A1 | 3/2018 | Abiad et al. |
| 2019/0038646 A1 | 2/2019 | Bright et al. |
| 2019/0300583 A1 | 10/2019 | Jarpe |
| 2020/0239528 A1 | 7/2020 | Binz et al. |
| 2021/0060144 A1 | 3/2021 | Brooks et al. |
| 2021/0187063 A1 | 6/2021 | Williams |
| 2022/0143158 A1 | 5/2022 | Abumrad et al. |

FOREIGN PATENT DOCUMENTS

| | | | |
|---|---|---|---|
| JP | 2012107051 A | 6/2012 | |
| KR | 20100032982 A | 3/2010 | |
| KR | 20150126979 A | 11/2015 | |
| WO | WO 95/28171 A1 | 10/1995 | |
| WO | WO 00/10598 A1 | 3/2000 | |
| WO | WO2010013495 A1 | 2/2010 | |
| WO | WO2011084507 A1 | 7/2011 | |
| WO | 2012134897 A1 | 10/2012 | |
| WO | WO2014184746 A1 | 11/2014 | |
| WO | 2018172264 A1 | 9/2018 | |
| WO | WO 2018172264 * | 9/2018 | ............ A61K 38/48 |
| WO | 2019126542 A1 | 6/2019 | |
| WO | WO2019145577 A1 | 8/2019 | |
| WO | WO2020110458 A1 | 6/2020 | |
| WO | 2022183064 A1 | 9/2022 | |

OTHER PUBLICATIONS

Niebroj-Dobosz & Janik, Acta Neurol Scand. 1999; 100: 6-11 (Year: 1999).*

Pugh KR et al, Abstract—"Glutamate and choline levels predict individual differences in reading ability in emergent readers", J.Neurosci. Mar. 12, 2014;34(11):4082-9. doi: 10.1523/JNEUROSCI. 3907-13.2014 https://www.ncbi.nim.nih.gov/pubmed/24623786 (Dec. 13, 2019).

Mayo clinic article, "Autism Spectrum Disorder", Symptoms and Causes, 5 pages (Year: 2019)downloaded on Dec. 23, 2019 from: https://www.mayoclinic.org/diseases-conditions/autism-spectrum-disorder/symptoms-causes/syc-20352928?p=1.

The Machine Translation of WO2010013495, English Abstract,"Pharmaceutical Composition Containing Highly Purified Botulinum Neurotoxin Therapeutic Agent as Active Ingredient, and Use Thereof", Akaike et al.; Feb. 4, 2010 (Year: 2010).

Nair et al., "Impaired Thalamocortical Connectivity in Autism Spectrum Disorder: A Study of Functional and Anatomical Connectivity", Brain, Journal of Neurology, 2013; 136: 1942-1955 (Year: 2013).

Panju et al., "Atypical Sympathetic Arousal in Children Wth Autism Spectrum Disorder and Its Association With Anxiety Symptomatology", Molecular Autism (2015) 6:64, pp. 1-10 (Year: 2015).

Saunte et al., "Improvement in Reading Symptoms Following Botulinwn Toxin A injection for Convergence Insufficiency Type Intermittent Exotropia", Acta Ophthalmologica (1755375X). Aug. 2015, vol. 93 Issue 5, pp. 1-3 (Year: 2015).

The WebMD website, "Treatments for Dyslexia", The International Dyslexia Association. National Center for Learning Disabilities. National Center for Neurological Disorders and Stroke, https://www.webmd.com/children/dyslexia-treatments; accessed Jun. 22, 2020 , 1 page, (Year: 2020).

Hulme et al., "Reading Disorders and Dyslexia", Current Opinion Pediatrics2016, 28: pp. 731-735 (Year: 2016) www.co-pediatrics.com.

Mazzone et al., "Vaginal Afferent Innervation of the Airways in Health and Disease", Physiol Rev 96: 975-1024, 2016, pp. 975-1024, (Year: 2016).

Schematic of innervation of organs, available from https://ars.els-cdn.com/content/image/3-s2.0-B9780323378048000055-f005-001 -9780323378048.jpg, downloaded Jun. 22, 2020 and reproduced within the Office action (Year: 2020).

The Harvard Medical School , "Cardiac Arrhythmias", Harvard Health Publishing, Published Feb. 2019, website; downloaded Jul. 18, 2020 from: https://www.health.harvard.edu/a_to_z/cardiac-arrhythmias-a-to-z; 5 pages total (Year: 2020).

Machine English Translation of the foreign patent document, KR20100032982, 7 pages total (Year: 2010).

Mitchell and Borasio et al., "Amyotrophic Lateral Sclerosis", Seminar, Lancet 2007; vol. 369: 2 pages 2031-2041 (Year: 2007).

Oomens and Forouzanfare t al., "Pharmaceutical Management of Trigeminal Neuralgia in the Elderly", Review Article Drugs Aging (2015) 32: pp. 717-726 (Year: 2015).

S. Kumar, "The Emerging Role of Botulinum Toxin in the Treatment of OroFacial Disorders: Literature Update", Asian Journal Pharm Clin Res, vol. 10, Issue 9, 2017, pp. 21-29 (Year: 2017).

Lewitt and Trosch, et al., "Idiosyncratic Adverse Reactions to Intramuscular Botulinum Toxin Type A Injection", Movement Disorders, 1997; 12: pp. 1064-1067 (Year: 1997).

Squires et al., "The Use of Botulinum Toxin Injections to Manage Drooling in Amyotrophic Lateral Scierosis/Motor Neurone Disease: A Systematic Review", Dysphagia (2014) 29: pp. 500-508 (Year: 2014).

The website downloaded on Jul. 2, 2020 from Juvenile Amyotrophic Lateral Sclerosis,Genetic and Rare Diseases Information Center (GARD)—an NCATS Program, https://rarediseases.info.nih.gov/diseases/11901/juvenile-amyotrophic-lateral-scierosis; Jul. 2, 2020, 8 pages total (Year: 2020).

Mortazavi et al., "Xerostomia Due to Systemic Disease: A Review of 20 Conditions and Mechanisms", Ann Med Health Sci Res. Jul.-Aug. 2014; 4(4): 503-510. doi: 10.4103/2141-9248.139284: 10.4103/2141-9248.139284 (Year: 2014).

The website downloaded Jul. 21, 2020 from Children's Hospital of Pittsburgh , "Cirrhosis in Children: Symptoms and Treatment", UPMC, 4 pages total . Jul. 21, 2020 (Year: 2020) (https://www.chp.edu/our-services/transplant/liver/education/liver-disease-states/cirrhosis.

Frank CT Smith, "Hyperhidrosis", Vascular Surgery—II, 2013; 31: pp. 251-255; doi: https://doi.org/10.1016/j.mpsur.2013.03.005 (Year: 2015).

(56) References Cited

OTHER PUBLICATIONS

Fernandez-Rodriguez et al., "Plasma Levels of Substance P in Liver Cirrhosis: Relationship to the Activation of Vasopressor Systems and Urinary Sodium Excretion", Hepatology, Jan. 1995; 21: pp. 35-40,(Year: 1995).
Glatte et al., "Architecture of the Cutaneous Autonomic Nervous System", Frontiers in Neurology, vol. 10, Article 970, Sep. 2019, pp. 1-11, 10: doi: 10.3389/fneur.2019.00970 (Year: 2019).
Web Article: Neuroscience, what-when-how, In Depth Tutorials and Information, Gross Anatomy of the Brain, Dec. 7, 2020, 2 pages, The autonomic system schematic downloaded Nov. 23, 2020 from http://what-when-how.com/neuroscience/the-autonomic-nervous-system-integrative-systems-part-1/; the image is reproduced in the Office action (Year: 2020).
WebMD, ADHD and Dyslexia: How to Tell Them Apart, Dyslexia and ADHD Similarities and Differences, Nov. 30, 2020, 3 pages, The article downloaded Nov. 30, 2020 from https://www.webmd.com/add-adhd/adhd-dyslexia-tell-apart?print=true; 3 pages total (Year: 2020) WebMD.
Chien et al., "Sympathetic Fiber Sprouting in Chronically Compressed Dorsal Root Ganglia Without Peripheral Axotomy", NIH Public Access, Author Manuscript of J. Neuropathic Pain Symptom Palliation. 2005; 1 (1 ): pp. 19-23 (Year: 2005).
Scott and Fryer, "Role of Parasympathetic Nerves and Muscarinic Receptors in Allergy and Asthma", NIH Public Access, Author Manuscript of Chem Immunol Allergy. 2012; 98: pp. 48-69 (Year: 2012).
Web Article, The image downloaded Dec. 4, 2020 from https://nursing-skills.blogspot.com/2014/01/angle-of-injection.html; image reproduced in Office action (Year: 2020.
Dobrek and Thor, "Glutamate NMDA Receptors in Pathophysiology and Pharmacotherapy of Selected Nervous System Dseases", Postepy Hig Med Dosw (online), 2011; 65: pp. 338-346 , 1 Year: 2011).
Erle CH Lim, "Botulinum toxin, Quo Vadis?", Elsevier Ltd., Medical Hypotheses (2007) 69, pp. 718-723 (Year: 2007) http://inti.elsevierhealth.com/ journals/ mehy.
International Search Report and Written Opinion, PCT/US2020/056206, dated Feb. 1, 2021.
Vacca et al., "Botulinum Toxin A Increases Analgesic Effects of Morphine, Counters Development of Morphine Tolerance and Modulates Glia Activation and μ Opioid Receptor Expression in Neuropathic Mice", Brain, Behavior, and Immunity 32 (2013), pp. 40-50 (Year: 2013).
Ryan J. Diel, MD et al, "Photophobia and sensations of dryness in migraine patients occur independent of baseline tear volume and improve following botulinum toxin A injections", HHS Public Access, Br J Ophthalmol. Author manuscript; available in PMC Aug. 1, 2019, pp. 1-15.
Donald C. Rojas, "The role of glutamate and its receptors in autism and the use of glutamate receptor antagonists in treatment", J Neural Transm. Aug. 2014 ; 121(8): 891-905, pp. 1-24.
Juan M. Espinosa-Sanchez et al, "New insights into pathophysiology of vestibular migraine", Frontiers in Neurology, Feb. 2015 | vol. 6 | Article 12, pp. 1-6.
Colleen Doherty, MD, "The Link Between Migraines and Tinnitus, Buzzing or ringing in your ears could be related to your episodes", VeryWell Health, Aug. 6, 2019, pp. 1-13 https://www.verywellhealth.com/link-between-migraines-and-tinnitus-4077631.
K,J. Powell et al, "The Role of CGRP in the Development of Morphine Tolerance and Physical Dependence", 4th International Meeting on Calcitonin Gene-Related Peptide (CGRP), The ScientificWorld (2001) 1 (S1), 21. 2 pages.
International Search Report and Written Opinion for International Patent Application No. PCT/US2021/032114, dated Sep. 10, 2021, 14 pages.
International Search Report and Written Opinion for International Patent Application No. PCT/2021/032116, dated Sep. 10, 2021, 14 pages.
Veenstra-Vander Weele et al., Neuropsychopharmacology (2017) 42, 1390-1398; doi:10.1038/npp.2016.237 (2017).
Shimmura et al., PLoS One 6(10): e25340. doi:10.1371/journal.pone.0025340 (2011).
Kandel, Schwartz and Jessell, "Principles of Neural Science", Third Edition, by Simon & Schuster, 1991; p. 218 (1991).
Fleischmann et al., "Nitrous oxide may not increase the risk of cancer recurrence after colorectal surgery: a follow-up of a randomized controlled trial" BMC Anesthesiology, 9 pages (2009).
Harley Academy, "Understanding Different Types of Botulinum Toxin A," 5 pages (2021).
Hart et al., "Chronic Pancreatitis: Managing a Difficult Disease," Am. J. Gastroenterol., 115(1), pp. 49-55 (2020).
Herner et al., "Glutamate increases pancreatic cancer cell invasion and migration via AMPA receptor activation and Kras-MAPK signaling," Int. J. Cancer, 129(10), pp. 2349-2359 (2011).
Mayo Clinic, "Epilepsy," available online at: <https://www.mayoclinic.org/diseases-conditions/epilepsy/diagnosis-treatment/drc-20350098>, 8 pages (2022).
Monroy et al., "The Use of Botulinum Toxin-A in the Treatment of Severe Bruxism in a Patient with Autism: A Case Report," Special Care in Dentistry, 26(1), pp. 37-39 (2006).
Park and Park, "Botulinum Toxin for the Treatment of N europathic Pain," Toxins, 9(260), 15 pages (2017).
Ristic, "7 Proven Roles of Substance P and Its Associated Diseases," available online at: https//supplements.selfdecode.com/blog/substance-p-roles/>, 9 pages (2021).
Sadick, "Botulinum toxin type B," (Abstract) Dermatol. Surg., 29(4), pp. 348-350 (2003).
Sarawagi et al., "Glutamate and GABA Homeostasis and Neurometabolism in Major Depressive Disorder," Frontiers in Psychiatry, 12(637863), pp. 1-16 (2021).
Strobl et al., "Best Clinical Practice in Botulinum Toxin Treatment for Children with Cerebral Palsy," Toxins, 7, pp. 1629-1648 (2015).
Trizna, "Dermatologic Use of Botulinum Toxin," available online at emedicine.medscape.com; 10 pages (2019).
Wijesekera and Leigh, "Amyotrophic lateral sclerosis," Orphanet Journal of Rare Diseases, 4(3), 22 pages (2009).

\* cited by examiner

TREATMENT OF AMYOTROPHIC LATERAL SCLEROSIS USING BOTULINUM TOXIN

CROSS-REFERENCE TO RELATED APPLICATIONS

1. This application is a continuation of and claims priority under 35 U.S.C. § 120 to U.S. patent application Ser. No. 16/875,947, filed May 15, 2020, which is a continuation-in-part of and claims priority under 35 U.S.C. § 120 to U.S. patent application Ser. No. 16/657,933, filed Oct. 18, 2019, now U.S. Pat. No. 10,722,552, and U.S. patent application Ser. No. 16/657,950 filed Oct. 18, 2019. The contents of each prior application in its entirety is expressly incorporated herein by reference thereto.
2. This application is a continuation of and claims priority under 35 U.S.C. § 120 to U.S. patent application Ser. No. 16/875,924, filed May 15, 2020, which is a continuation-in-part of and claims priority under 35 U.S.C. § 120 to U.S. patent application Ser. No. 16/657,933, filed Oct. 18, 2019, now U.S. Pat. No. 10,722,552, and U.S. patent application Ser. No. 16/657,950 filed Oct. 18, 2019. The contents of each prior application in its entirety is expressly incorporated herein by reference thereto.
3. This application is a continuation of and claims priority under 35 U.S.C. § 120 to U.S. patent application Ser. No. 16/875,935, filed May 15, 2020, which is a continuation-in-part of and claims priority under 35 U.S.C. § 120 to U.S. patent application Ser. No. 16/657,933, filed Oct. 18, 2019, now U.S. Pat. No. 10,722,552, and U.S. patent application Ser. No. 16/657,950 filed Oct. 18, 2019. The contents of each prior application in its entirety is expressly incorporated herein by reference thereto.
4. This application is a continuation of and claims priority under 35 U.S.C. § 120 to U.S. patent application Ser. No. 16/875,945, filed May 15, 2020, which is a continuation-in-part of and claims priority under 35 U.S.C. § 120 to U.S. patent application Ser. No. 16/657,933, filed Oct. 18, 2019, now U.S. Pat. No. 10,722,552, and U.S. patent application Ser. No. 16/657,950 filed Oct. 18, 2019. The contents of each prior application in its entirety is expressly incorporated herein by reference thereto.
5. This application is a continuation of and claims priority under 35 U.S.C. § 120 to U.S. patent application Ser. No. 16/875,951, filed May 15, 2020, which is a continuation-in-part of and claims priority under 35 U.S.C. § 120 to U.S. patent application Ser. No. 16/657,933, filed Oct. 18, 2019, now U.S. Pat. No. 10,722,552, and U.S. patent application Ser. No. 16/657,950 filed Oct. 18, 2019. The contents of each prior application in its entirety is expressly incorporated herein by reference thereto.
6. This application is a continuation of and claims priority under 35 U.S.C. § 120 to U.S. patent application Ser. No. 17,204,922, filed Mar. 17, 2021, which is a continuation of and claims priority under 35 U.S.C. § 120 to U.S. patent application Ser. No. 16/875,912, filed May 15, 2020, which is a is a continuation-in-part of and claims priority under 35 U.S.C. § 120 to U.S. patent application Ser. No. 16/657,933, filed Oct. 18, 2019, now U.S. Pat. No. 10,722,552, and U.S. patent application Ser. No. 16/657,950 filed Oct. 18, 2019. The contents of each prior application in its entirety is expressly incorporated herein by reference thereto.
7. This application is a continuation of and claims priority under 35 U.S.C. § 120 to U.S. patent application Ser. No. 16/995,042, filed Aug. 17, 2020, which is a continuation of and claims priority under 35 U.S.C. § 120 to U.S. patent application Ser. No. 16/657,950 filed Oct. 18, 2019. The contents of each prior application in its entirety is expressly incorporated herein by reference thereto.

FIELD OF THE INVENTION

The present invention generally relates to a method for treating Amyotrophic Lateral Sclerosis (ALS), also known as motor neuron disease (MND) or Lou Gehrig's disease using botulinum toxin.

BACKGROUND OF THE INVENTION

Amyotrophic Lateral Sclerosis (ALS), also known as motor neuron disease (MND) or Lou Gehrig's disease, causes the death of neurons controlling voluntary muscles. The term motor neuron disease can also be used for a group of conditions of which ALS is the most common ALS is characterized by stiffness, twitching, and weakness of muscles and their decrease in size. This disease may begin with weakness in the arms or legs, or with difficulty speaking or swallowing. About half of the people affected develop at least mild difficulties with behavior and thinking, and most experience pain as well. Most who suffer from the disease eventually lose the ability to walk, use their hands/extremities, speak, swallow, and breathe. There are three types of ALS categorized by where the symptoms first start: (1) limb onset, (2) trunk onset that affects the breathing muscles, and (3) bulbular onset that affects speech and swallowing first. In all of the types, the condition eventually spreads to the other muscles and paralyzes them. The underlying mechanism involves damage to both upper and lower motor neurons. The diagnosis is based on a patient's symptoms, with testing done to rule out other potential causes.

The data indicate that in 90-95% of cases the cause is unknown but it is believed to involve both genetic and environmental factors. In the remaining 5-10% of cases, the condition is understood to be inherited. About half of these genetic cases are due to one of two specific genes.

So far, there is no known cure for ALS. The goal of current treatment is to improve symptoms. A medication called Riluzole may extend the life of a patient by about 2-3 months. Non-invasive ventilation may result in both improved quality and length of life. Mechanical ventilation can prolong survival but does not stop the progression of the disease. A feeding tube may also help. The disease can affect people of any age, but usually signs begin around age 60, or age 50 in inherited cases. The average survival from onset to death is 2-4 years, though this can vary based on factors such as the level and quality of medical care. About 10% of patients survive longer than 10 years and most such patients eventually die from respiratory failure. In Europe, the disease affects about 2-3 people per 100,000 per year. Rates in much of the world are unclear. In the United States, it is more common in white people than black people. Current known treatments only help with symptoms until a patient dies.

What is needed therefore is a novel method for treating Amyotrophic Lateral Sclerosis (ALS), also known as motor neuron disease (MND) or Lou Gehrig's disease, that will stop the progressive death of motor neurons once ALS is diagnosed.

SUMMARY OF THE INVENTION

The claimed invention relates to a method for treating Amyotrophic Lateral Sclerosis (ALS), also known as motor neuron disease (ND) or Lou Gehrig's disease, in a patient in need thereof, comprising administering botulinum toxin to the patient, thereby treating the Amyotrophic Lateral Sclerosis (ALS). The administration of the botulinum toxin prevents an overproduction of glutamate, Substance P, and CGRP in a sensory system and thereby inhibits a migration of the glutamate, Substance P, and CGRP to the motor system. The botulinum toxin may be administered by subcutaneous or intradermal injection. The subcutaneous or intradermal injection may be administered to and/or around a vicinity of a trigeminal nerve of the patient.

The selected trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof. The subcutaneous or intradermal injection may be administered by subcutaneous or intradermal injection to and/or around a vicinity of a cervical nerve of the patient. The selected cervical nerve comprises the c-2 nerve, c-3 nerve, c-4 nerve, c-5 nerve, c-6 nerve, c-7 nerve, c-8 nerve, or a combination thereof. The subcutaneous or intradermal injection may be administered by subcutaneous or intradermal injection to and/or around a vicinity of a thoracic nerve of the patient. The selected thoracic nerve comprises the t-2 nerve, t-3 nerve, t-5 nerve, t-6 nerve, t-7 nerve, t-8 nerve, t-9 nerve, t-10 nerve, t-11 nerve, t-12 nerve, or a combination thereof. The subcutaneous or intradermal injection may be administered to and/or around the vicinity of a lumbar nerve of the patient. The selected lumbar nerve comprises an l-1 nerve, l-2 nerve, l-3 nerve, l-4 nerve, l-5 nerve, or a combination thereof. The subcutaneous or intradermal injection may be administered to and/or around the vicinity of a sacral nerve of the patient. The selected sacral nerve comprises the s-1 nerve, s-2 nerve, s-3 nerve, s-4 nerve, s-5 nerve, or a combination thereof. The subcutaneous or intradermal injection may be administered to and/or around a vicinity of a nerve comprising a thoracic nerve, a lumbar nerve, a sacral nerve, or a combination thereof of the patient. The administering may comprise by subcutaneous or intradermal injection 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the l-1 to l-2, l-2 to l-3, and/or l-4 to l-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral). The botulinum toxin used in the treatment in accordance with embodiments of the present invention comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof. In further embodiments, a total dosage of the botulinum toxin administered for an adult who weighs about 150 lbs is between about 1 unit and about 150 units. A total dosage of the botulinum toxin for an adult or a child is adjusted for age, weight, or a combination thereof.

DETAILED DESCRIPTION OF THE PREFERRED EMBODIMENTS

Further in relation to this, before explaining at least the preferred embodiments of the invention in greater detail, it is to be understood that the invention is not limited in its application to the details of construction and to the arrangements of the components set forth in the following description. It would be understood by those of ordinary skill in the art that embodiments beyond those described herein are contemplated, and the embodiments can be practiced and carried out in a plurality of different ways. Also, it is to be understood that the terminology used herein is for the purpose of description and should not be regarded as a limiting factor.

Unless otherwise defined, the terms used herein refer to that which the ordinary artisan would understand such term to mean based on the contextual use of such term herein. To the extent that the meaning of a term used herein as understood by the ordinary artisan based on the contextual use of such term differs in any way from any particular dictionary definition of such term, it is intended that the meaning of the term as understood by the ordinary artisan will prevail.

As used herein, the term "about" means approximately or nearly and in the context of a numerical value or range set forth herein means ±10% of the numerical value or range recited or claimed.

The term "treating" includes delaying, alleviating, mitigating or reducing the intensity, progression, or worsening of one or more attendant symptoms of a disorder or condition and/or alleviating, mitigating or impeding one or more causes of a disorder or condition. Treatment under the claimed invention may be a preventative treatment, prophylactic treatment, remission of treating or ameliorating treatment.

The term "therapeutically effective amount" or "therapeutically effective dose" refers to the amount of a composition, compound, therapy, or course of treatment that, when administered to an individual for treating a disorder or disease, is sufficient to effect such treatment for the disorder or disease. The "therapeutically effective amount" will vary depending on the composition, the compound, the therapy, the course of treatment, the disorder or disease and its severity and the age, weight, etc., of the individual to be treated.

The term "unit" refers to the amount of botulinum toxin needed to kill 50% of a group of 18-20 gm female Swiss-Webster mice given the injection intraperitoneally.

The term "vicinity of a nerve" refers to anywhere on the dermatome involved with the nerve.

In accordance with the principles of the present invention, use of botulinum toxin to treat a variety of symptoms is provided.

Mechanism of Action of Botulinum Toxin

Botulinum toxins cleave and destroy a protein called synaptosomal nerve-associated protein 25 ("SNAP25") and/or synaptobrevin (also called vesicle-associated membrane protein ["VAMP"]). Botulinum toxins A, C, and E cleave SNAP25 at different locations, but the effect is in general the same—the protein is destroyed and cannot function until the cell makes new ones. Botulinum toxins B, D, F and G cleave VAMP present at the cytoplasmic surface of the synaptic vesicle. The two important locations in the body where the proteins are found are at the terminals of the motor neurons (muscle) and in the cell membranes of astrocytes, glial cells, and satellite cells. These three cell types surround sensory neurons and form part of the blood-brain barrier. In motor nerves, to cause them to fire, vesicles of acetylcholine move from inside the motor neuron across the cell membrane at the synapse between the motor nerve and muscle fiber. Acetylcholine is released into the synapse and activates receptors in the muscle fiber, which contracts the muscle fiber. In sensory nerves, when a nerve is damaged from physical or mental injuries, the three aforementioned structural cells produce large amounts of Substance P, Calcitonin Gene Related Peptide (CGRP), and glutamate internally and the molecules are moved by vesicles to the cell membrane where the SNAP25 and/or VAMP moves the molecules through the cell membrane and releases the molecules into the cerebrospinal fluid that surrounds the neurons. There, the molecules bind to the receptor on the sensory nerves, causing the neuroexcitatory effects. The molecules can also diffuse in the cerebral spinal fluid (CSF) and influence other sensory nerves to become hyperactive, a process called central sensitization.

This mechanism of cleaving the SNAP25 and/or VAMP in muscles and sensory nerves causes the only known clinical effects of botulinum, which paralyzes muscles in the motor system for 3-4 months until the cell grows a new protein. This effect has been used for decades for overactive muscles (such as to treat overactive muscles as part of cervical dystonia, blepharospasm, tic, Parkinson's, cerebral palsy, etc.), wrinkles in the face, excessive sweating, and overactive bladder.

In the sensory nerves, the mechanism has been used for migraines and depression. The effect of blocking the SNAP25 and/or VAMP in the glial, satellite, and astrocyte cells will work for 5-9 months until these cells grow new proteins. The important part of this mechanism is that the botulinum effect does not destroy cells and does not stop the normal production of or effects of acetylcholine (muscles) or Substance P, CGRP, or glutamate in sensory nerves. These facts give huge advantages over a monoclonal antibody which would eliminate all glutamate, CGRP, and Substance P. Side effects of such elimination would be disastrous. The receptor antagonists also have problems—for example, because the receptor antagonists are not site-specific, they block glutamate, Substance P, and CGRP everywhere. Too little glutamate, Substance P, and CGRP is a problem, as well as too much. It is difficult to regulate oral or I.V. doses to obtain the correct level of reduction in areas that are too high in glutamate, Substance P, and/or CGRP without over-reduction in areas with normal levels.

Small doses of botulinum toxin injected into a specific muscle can cleave SNAP25 and/VAMP to calm the muscle's overreaction or paralyze the muscle temporarily if desired. Or, if injected subcutaneously near unmyelinated sensory nerves, the botulinum toxin can stop the overproduction of the sensory neuroexcitatory compounds without affecting normal glutamate, Substance P, and CGRP production and function. It is, however, noted that botulinum toxin is highly lethal. Botulinum toxin is the most toxic poison known. One molecule of botulinum toxin destroys one protein molecule of SNAP25 and/or VAMP A little bit goes a long way. Its production, storage and injection must be done with knowledge and care.

Mechanism of Effect of Botulinum Toxin on Sensory Nerves

In particular, the mechanism of the sensory effect (stopping overproduction of glutamate, Substance P, and CGRP) is as follows: almost all nerves in the human body are surrounded by a protective coating called myelin, which protects the nerve and makes neural conduction faster. Botulinum toxin has difficulty penetrating the myelin. Just under the skin are sensory pain nerves called C-fibers, which are unmyelinated. Research has shown that very low dose botulinum toxin can penetrate these axons and diffuse up the axon to the cell body into the CSF and affect the SNAP25 and/or VAMP on the glial, satellite, and astrocyte cells. Subsequently, botulinum toxin destroys the SNAP25 and/or VAMP and prevents the release of the excess Substance P, CGRP, and glutamate, which is involved in a response mechanism to neural-injury without affecting normal glutamate, Substance P, and CGRP production, use, or receptors. An example of a malfunction with the normal nerve mechanism is an infection of a nerve by the shingles virus. The infection by the shingles virus damages the nerve but does not kill it, or there would be no feeling (numbness). This causes a spike in the production of glutamate, Substance P, and CGRP. This causes the well-known shingles pain and hypersensitivity. Over a 2-3 month period, the infection is controlled, the nerve heals, and the overproduction of the neuroexcitatory chemicals gets back to normal. However, sometimes for unknown reasons, the overproduction does not get back to normal but remains high, and severe chronic pain and hypersensitivity persists. Chronically overstimulated neurons can cause numerous problems depending on where the neurons are located. The neuroexcitatory chemicals can travel up the spinal cord to the brain in the CSF and affect neurons there. This process is called central sensitization. Depending on where glutamate, Substance P, and CGRP are produced and where the molecules travel to, the molecules can cause chronic pain, headaches, vertigo, sensitivity to light, sensitivity to touch, cold sensitivity, overactive bladder, depression, anxiety, flashbacks, mental fogginess, vasoconstriction of extremities, sleep disturbances, and perhaps the death and malformation of the developing neural architecture in children with ASD (autism).

Theory of the Cause of ALS

One of the leading theories for the cause of ALS is that elevated levels of glutamate over stimulate motor neurons. This causes the death of the motor neurons by a process called neuroexcitatory toxicity. The only drug that has shown to help extend life of ALS patients by 2-3 months is Riluzole, which is a glutamate receptor antagonist. It blocks the effects of glutamate. Motor neurons appear to be especially sensitive to overstimulation by glutamate which is not widely found in the motor system. The main neurotransmitter in motor neurons is acetylcholine. Glutamate is the main neurotransmitter in the sensory system. Motor nerves in the brain, spinal cord, and peripheral nerves are separated from sensory nerves. The cerebral cortex in the brain is sensory, while the cerebellum is motor. The sensory and motor nerves are segregated in the spinal cord, and exit the spinal cord separately at the dorsal root, which is sensory, and the ventral root, which is motor. Even when they come together to form mixed peripheral nerves, they are still separated.

Substances that make nerves fire with less stimulation are called "excitatory." Substances that make nerves require more stimulation to tire are called "inhibitory." Examples of neuroexcitatory substances are nicotine, cocaine, methamphetamine, epinephrine, and glutamate. Examples of neuroinhibitory substances are serotonin, gamma-aminobutyric acid (GABA), narcotics, and other medications such as Lyrica (for nerve pain) and Valium (an anxiolytic/sedative).

Too much inhibition of nerves can cause drowsiness and death. Too many excitatory compounds can cause nerves to fire much too fast with the possibility of resulting pain, lack of sleep, light sensitivity, cell death, seizures, etc. (symptoms depend on the function of the specific nerves).

If excess glutamate is overstimulating the motor nerves, where is it coming from and how can it be stopped from affecting the motor nerves without causing severe side effects in the sensory system? In the sensory system, when glutamate, Substance P, and CGRP, are overproduced, the result is migraines, fibromyalgia, and other neuropathic conditions. The source of the overproduction of glutamate is believed to be the neurostructural cells that surround the neurons. They are the glial, satellite, and astrocyte cells. The mechanism is that Substance P, CGRP (calcitonin gene-related peptide), and glutamate are produced intracellularly by the ribosomes of these cells, packaged in vesicles, and transported to the cell membrane. Here, a specialized protein called SNAP25 and/or VAMP transports it across the cell membrane and it is released into the CSF. They then act as ligands to the nerves and make them fire with less stimulation (neuroexcitation). The only other place the SNAP25 and/or VAMP is known to be functional in the human body is at the neuromuscular junction in muscle cells where it releases vesicles with acetylcholine into the neuromuscular junction and causes muscles to contract. In normal glutamate production in the cells, it is used internally in the neurons and not released by the SNAP25 and/or VAMP into the CS spaces.

Ideally, the sensory overproduction of glutamate, Substance P, and CGRP resulting from a neural injury is isolated from the motor system. Nature tries to achieve this, but it is less than a perfect isolation. This is in evidence from symptoms such as muscle spasms, TMJ spasms, trigger points, and muscle cramps that are found in migraines, fibromyalgia, and other neuropathic conditions. The excess glutamate, Substance P, and CGRP that are found in the blood, CSF and brain could reach the motor system though the muscle spindles. There is a direct interface between the sensory and motor nerves at the muscle spindles. This is used in the proprioception system. This system along with the vestibular canals and vision give us our system of balance and our knowledge of where our body parts are in three dimensions. ALS patients are known to have balance issues also. The excess glutamate in the brain and spinal fluid also affects the blood brain barrier. It causes the barrier to become "leaky" This is the source of the elevated blood levels in neuropathic conditions and could also be a source of elevated motor levels of glutamate Substance P, and CGRP. The source of overstimulation of the motor neurons being the muscle spindle interface would also explain how the motor neurons die one at a time and not in masses in particular areas or regions of the neurons. ALS patients present many symptoms of these sensory disturbances such as chronic pain, depression, anxiety, overactive bladder, etc.

The only muscles in the body not affected by ALS are the ocular motor muscles that move and focus the eyes. They are supplied with innervations by the cranial nerves 3, 4 6. ALS patients can always move and focus their eyes and it is used as a way for them to communicate as their paralysis progresses. Embryologically, when nerves and muscle fibers are connecting there are many neurons connecting to each muscle fiber. Through a process called neural pruning, all but one neural-muscle fiber connection is removed. The only muscles in the body where this process does not take place is the ocular motor muscles. The ocular motor muscles retain the multiple nerve connections to each muscle fiber. The multiple connections are retained to allow for fine control of visual tracking and focusing systems required for visual acuity. The pruning process of removing the excess neurons is a process of programmed cell death called apoptosis. The triggering of this process and its regulation is not well understood but it involves allowing excess calcium ions to enter the selected neurons and that triggers the apoptosis (death) of the neuron. Excess stimulation of sensory neurons from glutamate, Substance P, and CGRP is known to cause sensory neurons to die due to neuroexcitatory toxicity. This is caused by excess calcium ions entering the neurons due to the excess stimulation. It could be that the excess calcium ions that enter the motor neurons from the sensory system glutamate overstimulation are triggering the embryonic apoptosis pruning system.

Excess glutamate that over-stimulates the motor neurons causes a series of cellular events that lead to the death of the motor neurons. The overstimulation causes an excess influx of Ca+ (calcium ions) in the cells. This alters the pH of the cell to nonsurvivable levels. The motor neurons expend a lot of energy trying to buffer the effects of the excess Ca+ ions. This exhausts and damages the mitochondria. The mitochondrial damage and the altered intracellular pH activate the cellular apoptosis mechanism which causes cell death. There are genetic factors that have been found involving these mechanisms mentioned above that have been linked to ALS. It is logical that a genetic weakness in any of these systems would increase the probability of excess levels of glutamate causing cell death due to the over stimulation. If genetic problems were the cause of ALS, it can't explain why, at an earlier age, there is not any damage. The age of onset is between 50 and 60 with incidence rising with age.

Although not wishing to be bound by a specific theory, the following factors are believed to lead to the development of ALS: (i) age and the reduced healing ability of nerves, muscles, and the whole body in general; (ii) genetic, the less than ideal isolation of the sensory and motor systems especially in the muscle spindles leads to a spill-over of glutamate, especially if it is being overproduced by the sensory structural cells in connection with neuropathic conditions such as fibromyalgia, migraines, anxiety, depression, etc.; (iii) genetic defects that affect the Ca+ buffering system that works to stop cellular damage from overstimulation by glutamate; (iv) genetic defects in the system of apoptosis that make the cell more likely to die from cellular suicide in response to the altered pH, mitochondrial damage, and altered protein folding resulting from the altered pH; (v) genetic defects in the cellular energy producing systems of the cells that is involved in trying to buffer the altered pH; (vi) genetic defects in the ribosomes which are involved in cellular damage repair; (vii) overproduction of Glutamate, Substance P, and CGRP in the sensory system; and (viii) leakage in the blood brain barrier caused by excess brain and CSF glutamate, Substance P, and CGRP, the source of which is overproduction from the sensory system.

Treatment

Subcutaneous and/or intradermal botulinum toxin injections in the trigeminal, cervical, thoracic, lumbar, and/or sacral areas can treat ALS. Botulinum toxin treatment is currently contraindicated in ALS patients for the muscle spasms as injections into motor neurons would cause temporary (3-4 months) paralysis and paralysis is the problem in ALS. Our innovative injection techniques should minimize or eliminate and motor side effects while still stopping the sensory overproduction of Glutamate, Substance P, and CGRP. It will only affect overproduction of glutamate, Substance P, and CGRP in the sensory nerve when used in these doses subcutaneously or intradermally, which inhibits the migration of the glutamate, Substance P, and CGRP from the sensory nerve to the motor system.

The methods according to embodiments of the present invention are novel and inventive as they allow for a minimal amount of botulinum toxin to be injected and still cover all dermatomes with no or minimal motor involvement. By using a subcutaneous or intradermal injection that reaches the unmyelinated C-fibers, it takes a lot less botulinum toxin to absorbed into them as opposed to the myelinated nerves, and there are no motor nerves in the epithelium. Also, the injection at, for example, ½ to 1 inch from the patient's spine allows for a lower dose of botulinum toxin because there is a shorter distance to the dorsal root ganglia (approximately ¼ inch) for botulinum toxin to diffuse as compared to several feet if given in arm or leg. The site is the only place in the body where the sensory and motor nerves are not in close proximity. This combination of low dose and separation of approximately 1 inch of bone and tissue between the motor and sensory nerves should minimize or eliminate any motor side effects. Furthermore, the methods according to embodiments of the present invention preferably do not require vagus nerve injection. The only superficial exposure of the vagus nerve is Arnold's nerve which is in the ear canal. It is a mixed motor and sensory nerve, and the motor component of it innervates the throat. If you inject botulinum toxin to or around the Arnold's nerve, you can generate speech and swallowing problems. The inventor(s) have found that there is enough anastomosis between the sensory cervical nerves, the trigeminal nerve and the vagus nerve that botulinum toxin can reach the vagus ganglia and stop the overproduction of Substance P, glutamate, and CGRP.

The subcutaneous or intradermal injection may be administered to and/or around a vicinity of a trigeminal nerve of the patient. The selected trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof. In the facial dermatome, botulinum toxin is injected subcutaneously to the trigeminal nerve or around the vicinity of the trigeminal nerve because the trigeminal nerve is entirely sensory. In contrast, the facial nerve supplies motor innervations to the face and has no subcutaneous axons. Thus, injecting botulinum toxin to the trigeminal nerve minimizes or eliminates muscular side effects. The subcutaneous or intradermal injection may be administered by subcutaneous or intradermal injection to and/or around a vicinity of a cervical nerve of the patient. The selected cervical nerve comprises the c-2 nerve, c-3 nerve, c-4 nerve, c-5 nerve, c-6 nerve, c-7 nerve, c-8 nerve, or a combination thereof. The subcutaneous or intradermal injection may be administered by subcutaneous or intradermal injection to and/or around a vicinity of a thoracic nerve of the patient. The selected thoracic nerve comprises the t-2 nerve, t-3 nerve, t-5 nerve, t-6 nerve, t-7 nerve, t-8 nerve, t-9 nerve, t-10 nerve, t-11 nerve, t-12 nerve, or a combination thereof. The subcutaneous or intradermal injection may be administered to and/or around the vicinity of a lumbar nerve of the patient. The selected lumbar nerve comprises an 1-1 nerve, 1-2 nerve, 1-3 nerve, 1-4 nerve, 1-5 nerve, or a combination thereof. The subcutaneous or intradermal injection may be administered to and/or around the vicinity of a sacral nerve of the patient. The selected sacral nerve comprises the s-1 nerve, s-2 nerve, s-3 nerve, s-4 nerve, s-5 nerve, or a combination thereof. The subcutaneous or intradermal injection may be administered to and/or around a vicinity of a nerve comprising a thoracic nerve, a lumbar nerve, a sacral nerve, or a combination thereof of the patient. It is not or may not be necessary to inject botulinum toxin to the cranial nerves because there is numerous anastomosis between the trigeminal nerves and the spinal nerves. The administering may comprise, by subcutaneous or intradermal injection, injecting 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the 1-1 to 1-2, 1-2 to 1-3, and/or 1-4 to 1-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral). While the administration site is about one-inch lateral to the patient's spine in the above embodiment, the distance can be more than 0 inches, about 0.1-3 inches, about 0.5-2.5 inches or about 1.0-2.0 inches. Alternatively, the distance can be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0 inches. The methods according to embodiments of the present invention are preferably applied to all or many of these locations. Depending on symptoms or conditions, the botulinum toxin used in embodiments of the present invention can be injected to a subset or subgroup of the locations described in embodiments of the present invention. In one embodiment, 3 injections of 2 units each distributed along each side of the neck in the cervical area on the trigeminal nerve, 1 injection of 2 units in the ophthalmic, maxillary, and/or mandibular division subcutaneously and bilaterally. These dosages are for an adult who weighs about 150 lbs. The dosage for younger children with ALS would have to be adjusted for age and weight.

Botulinum toxin is given to lower the levels of Substance P, CGRP, and glutamate, and botulinum toxin normally begins to work after about three days. It normally takes the botulinum toxin about one to two weeks to reach the height of its effectiveness. For example, blood glutamate levels can be monitored to make sure that the levels drop to normal, and the patient's physical symptoms can be monitored to make sure the levels normalize as well. Normal blood glutamate levels are known to range from 40 to 60 uM. Alternatively, normal blood glutamate levels may be one a person skilled in the art would reasonably perceive. When the botulinum toxin wears off, blood tests show an increase in Substance P, glutamate, or CGRP, and/or the symptoms begin to redevelop, more botulinum toxin can be given to combat the symptoms of the condition. If levels/symptoms fail to normalize, then perhaps a small dose of one of the glutamate antagonists can be administered to help lower glutamate levels without producing side effects. For patients, as discussed, it is possible to use the claimed method to delay, alleviate, mitigate or reduce the intensity, progression, or worsening of one or more attendant symptoms of a disorder or condition, and/or the claimed method alleviates, mitigates or impedes one or more causes of a disorder or condition.

In general, the total dosage can be about 1-150 units depending on the patient's body weight. Preferably, the total dosage is about 50-150 units. The total dosage for adults whose weight is about 150 lbs. is, for example, about 1-150 units. Preferably, the total dosage for adults whose weight is about 150 lbs is about 50-150 units. For children, the total dosage can be adjusted to the child's body weight and age.

The botulinum toxin used in the treatment in accordance with embodiments of the present invention comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof. In general, the therapeutically effective amount of the botulinum toxin administered is between about 1 unit and about 150 units. The dosage for adults is, for example, about 1-150 units. For children, the dosage can be adjusted to the child's body weight. If levels/symptoms fail to normalize, then if desired, a small dose of one of the glutamate antagonists can be administered to help lower glutamate levels without producing side effects.

Botulinum toxins for use according to the present invention can be stored in lyophilized vacuum dried form in containers under vacuum pressure or as stable liquids. Prior to lyophilization, the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Preferably, the botulinum neurotoxin is peripherally administered by administering it to or in the vicinity of the aforementioned nerve or to the aforementioned nerve branch or its ganglion nuclei. This method of administration permits the botulinum neurotoxin to be administered to and/or to affect select intracranial target tissues. Methods of administration include injection of a solution or composition containing the botulinum neurotoxin, as described above, and include implantation of a controlled release system that controllably releases the botulinum neurotoxin to the target trigeminal tissue. Such controlled release systems reduce the need for repeat injections. Diffusion of biological activity of botulinum toxin within a tissue appears to be a function of dose and can be graduated. Jankovic J., et al Therapy with Botulinum Toxin, Marcel Dekker, Inc., (1994), page 150. Thus, diffusion of botulinum toxin can be controlled to reduce potentially undesirable side effects that may affect the patient's cognitive abilities. For example, the botulinum neurotoxin may be administered so that the botulinum neurotoxin primarily effects neural systems believed to be involved in a selected neuropsychiatric disorder, and does not have negatively adverse effects on other neural systems.

In addition, the botulinum neurotoxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of botulinum neurotoxins that may not have a functional targeting moiety (e.g., a portion of the toxin that binds to a neurotoxin receptor, and/or a translocation domain). By way of example, and not by way of limitation, a fragment of botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its toxic effects within the cell. The pH of the target tissue is only temporarily lowered so that neuronal and/or glial injury is reduced.

The botulinum toxin used in the treatment in accordance with embodiments of the present invention comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof. Because of different mechanisms and cleavage sites of botulinum toxins, the potency, dosage, or duration may vary depend on the type of botulinum toxins. The botulinum toxin can be used with other modulating drugs or chemicals. In further embodiments, the therapeutically effective amount of the botulinum toxin administered is between about 1 unit and about 150 units.

In some embodiments, a composition administered to a patient consists of botulinum toxin(s). Alternatively, a pharmaceutically active composition contained in a composition administered to a patient consists of botulinum toxin(s). The composition may additionally include, but not be limited to, a pharmaceutically inactive excipient, stabilizer and/or carrier. If lyophilized, the botulinum toxin may be reconstituted with saline or water to make a solution or composition to be administered to the patient. Alternatively, a composition administered to a patient comprises botulinum toxin(s) and other pharmaceutically active ingredients.

Unless defined otherwise, all technical and scientific terms used herein have same meaning as commonly understood by the person of ordinary skill in the art to which this invention belongs.

It should be understood that the above description of the invention and specific examples, while indicating preferred embodiments of the present invention, are given by way of illustration and not limitation. Many changes and modifications within the scope of the present invention may be made without departing from the spirit thereof, and the present invention includes all such changes and modifications.

What is claimed is:

1. A method for treating Amyotrophic Lateral Sclerosis (ALS) in a patient in need thereof, comprising
   administering botulinum toxin to the patient, thereby treating the Amyotrophic Lateral Sclerosis (ALS), wherein the administering for an adult comprises, by subcutaneous or intradermal injection, injecting 1-4 units to and/or around the vicinity of a trigeminal nerve, 1-4 units to and/or around the vicinity of a cervical nerve, lateral to the patient's spine, 1-4 units to and/or around the vicinity of a thoracic nerve, lateral to the patient's spine, 1-4 units to and/or around the vicinity of a lumbar nerve, lateral to the patient's spine, and/or 1-4 units to and/or around the vicinity of a sacral nerve, lateral to the patient's spine, and
   monitoring if the patient's neuroexcitatory substances levels normalize.

2. The method of claim 1, wherein the trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof.

3. The method of claim 1, wherein the cervical nerve comprises a c-2 nerve, c-3 nerve, c-4 nerve, c-5 nerve, c-6 nerve, c-7 nerve, c-8 nerve, or a combination thereof.

4. The method of claim 1, wherein the thoracic nerve comprises a 1-2 nerve, t-3 nerve, t-5 nerve, t-6 nerve, t-7 nerve, t-8 nerve, 1-9 nerve, t-10 nerve, t-11 nerve, t-12 nerve, or a combination thereof.

5. The method of claim 1, wherein the lumbar nerve comprises an 1-1 nerve, 1-2 nerve, 1-3 nerve, 1-4 nerve, 1-5 nerve, or a combination thereof.

6. The method of claim 1, wherein the sacral nerve comprises an s-1 nerve, s-2 nerve, s-3 nerve, s-4 nerve, s-5 nerve, or a combination thereof.

7. The method of claim 1, wherein the administered botulinum toxin comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof.

8. The method of claim 1, wherein a total dosage of the botulinum toxin for an adult who weighs about 150 lbs. is between about 1 unit and about 150 units.

9. The method of claim 8, wherein a total dosage of the botulinum toxin for an adult, a child is adjusted for age, weight, or a combination thereof.

10. The method of claim 1, wherein the neuroexcitatory substances are substance P, calcitonin gene-related peptide (CGRP) or glutamate.

11. The method of claim 1, wherein the patient's neuroexcitatory substances level are blood levels.

12. The method of claim 1, wherein the monitoring if the patient's neuroexcitatory substances levels normalize comprises monitoring if the patient's blood glutamate level normalizes.

13. The method of claim 12, wherein a normal blood glutamate level is from about 40 to about 60 uM.

14. The method of claim 1, wherein if the patient's neuroexcitatory substances levels fail to normalize, additional botulinum toxin is administered to the patient.

15. The method of claim 14, wherein if the patient's neuroexcitatory substances levels fail to normalize even after administering the additional botulinum toxin, an antagonist to the neuroexcitatory substances is administered to the patient.

16. The method of claim 1, wherein if the patient's neuroexcitatory substances levels fail to normalize, an antagonist to the neuroexcitatory substances is administered to the patient.

17. The method of claim 1, wherein the monitoring if the patient's neuroexcitatory substances levels normalize occurs or two weeks after the administering botulinum toxin to the patient.

18. The method of claim 1, further comprising monitoring the patient's physical symptoms.

19. The method of claim 18, wherein if the patient's physical symptom continues, additional botulinum toxin or an antagonist to the neuroexcitatory substances is administered to the patient.

20. The method of claim 1, wherein each of the subcutaneous or intradermal injection is bilateral.

\* \* \* \* \*